(12) United States Patent
Alexakis

(10) Patent No.: US 11,229,723 B2
(45) Date of Patent: *Jan. 25, 2022

(54) BIOCOMPATIBLE MOLDED PART

(71) Applicant: Antonis Alexakis, Oehningen (DE)

(72) Inventor: Antonis Alexakis, Oehningen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/866,395

(22) Filed: May 4, 2020

(65) Prior Publication Data

US 2020/0330650 A1 Oct. 22, 2020

Related U.S. Application Data

(63) Continuation of application No. 15/544,872, filed as application No. PCT/EP2016/051042 on Jan. 19, 2016, now Pat. No. 10,639,401.

(30) Foreign Application Priority Data

Jan. 20, 2015 (DE) ...................... 10 2015 100 806.8

(51) Int. Cl.
| | |
|---|---|
| *A61L 27/58* | (2006.01) |
| *A61L 27/42* | (2006.01) |
| *A61L 2/00* | (2006.01) |
| *A61L 27/02* | (2006.01) |
| *A61L 27/16* | (2006.01) |
| *A61L 27/38* | (2006.01) |
| *A61F 2/30* | (2006.01) |

(52) U.S. Cl.
CPC ............ *A61L 27/58* (2013.01); *A61L 2/0035* (2013.01); *A61L 27/025* (2013.01); *A61L 27/16* (2013.01); *A61L 27/3847* (2013.01); *A61L 27/425* (2013.01); *A61L 27/427* (2013.01); *A61F 2/3099* (2013.01); *A61L 2202/21* (2013.01); *A61L 2430/02* (2013.01); *A61L 2430/12* (2013.01)

(58) Field of Classification Search
CPC .... A61L 27/16; A61L 27/3847; A61L 27/425; A61L 27/427; A61L 2430/02; A61L 2430/12; A61F 2/3099
See application file for complete search history.

(56) References Cited

U.S. PATENT DOCUMENTS

| | | |
|---|---|---|
| 4,619,655 A | 10/1986 | Hanker |
| 6,630,153 B2 | 10/2003 | Long |
| 6,905,516 B1 | 6/2005 | Lemaitre |
| 10,639,401 B2 * | 5/2020 | Alexakis ............... A61L 2/0035 |
| 2006/0127444 A1 | 6/2006 | Kuhn |
| 2009/0017095 A1 | 1/2009 | Barnouin |
| 2014/0120149 A1 | 5/2014 | Flynn |
| 2014/0335147 A1 | 11/2014 | Alexakis |

FOREIGN PATENT DOCUMENTS

| | | |
|---|---|---|
| DE | 102005060761 A1 | 6/2007 |
| EP | 2572738 A2 | 3/2013 |
| WO | 2013079443 A1 | 6/2013 |

OTHER PUBLICATIONS

Aragonite—Article from Wikipedia (Year: 2019).
Machine translation of DE 102005060761 AI (Year: 2019).
T. Miclau, L. E. Dahners, and R. W. Lindsey. In Vitro Pharmacokinetics of Antibiotic Release from Locally Implantable Materials. Journal of Orthopaedic Research, vol. 11, pp. 627-632 (1993). (Year: 1993).
Wikipedia entry for "Aragonite" (Year: 2018).

* cited by examiner

*Primary Examiner* — Michael P Cohen
(74) *Attorney, Agent, or Firm* — Loginov & Associates, PLLC; William A. Loginov

(57) ABSTRACT

The invention relates to a biocompatible molded part for supporting new bone formation, in particular the reformation of a jaw bone or a jaw bone portion in a mammal, preferably a human, wherein the molded part is suitable to be placed on the jaw bone and is designed as a solid body. The invention also relates to a composition for producing a biocompatible molded part, a method for producing a biocompatible molded part, a use of a biocompatible molded part and a kit comprising a plurality of molded parts.

20 Claims, 2 Drawing Sheets

BIOCOMPATIBLE MOLDED PART

Figure 1:
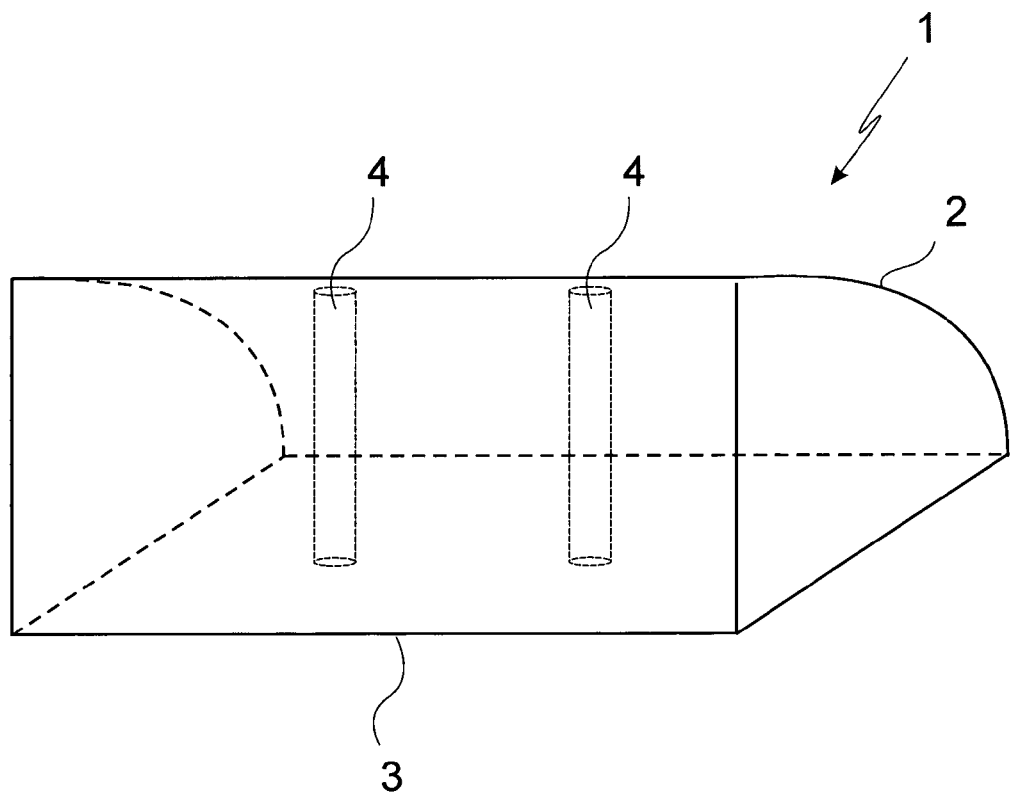

The invention relates to a biocompatible molded part for supporting new bone formation.

In medicine, there are numerous applications in which it is desirable for bone material to be newly formed by the human or animal patient itself. This applies in particular in dental medicine, if the jaw bone is attacked and partially destroyed, for example, by periodontitis.

For the targeted growth of osteoblasts on the human or animal jaw bone it is known to form cavities in a molded part. Osteoblasts can grow in these cavities and thereby fill bone defects or augment the height and/or width of the jaw. It has proved disadvantageous that, in particular in the event of relatively large lesions, some of these materials do not offer sufficient stability for satisfactory osteogenesis or ossification and moreover are reabsorbed too quickly and unevenly. As a result, the objective of filling or augmentation is often not met.

Although other materials are reabsorbed very slowly, they do not allow any more osteoblast growth in the upper layers, since because of the long residence time of the barrier there is no longer any nutrient medium available for the osteoblast growth.

Therefore, the object of the present invention is to overcome the disadvantages of the prior art and to provide a molded part which encourages osteoblast growth.

This object is achieved by a biocompatible molded part according to claim 1. Preferred embodiments of the invention are the subject of the dependent claims.

According to the invention a biocompatible molded body is provided, which serves to support the new bone formation, in particular the reformation of a jaw bone or of a jaw bone portion in a mammal, preferably in a human. In this case the molded part is suitable to be placed on a bone base, in particular the jaw bone. The biocompatible molded part according to the invention is formed as a solid body into which blood vessels and osteoblasts grow in the course of the treatment. Bone formation then takes place during the progressive reabsorption of the molded part. On the one hand, this solid body gives sufficient stability for the reformation of the jaw bone during the osteoblast growth, and on the other hand the solid body is designed in such a way that blood vessels and newly forming bone material can grow through it completely. Because of the biocompatibility, the osteogenesis is promoted by the solid body or the material forming it, and at the same time a stabilization of the jaw bone is achieved until the bone augmentation is concluded.

During use, i.e. in the course of the bone formation, the molded part or the solid body is reabsorbed little by little. This reabsorption is accompanied by a corresponding filling of the lesion with newly formed bone material or filling with osteoblasts which initiate or perform the osteogenesis.

Surprisingly it has been shown that the chosen block form advantageously supports the ossification or osteogenesis, since it is possible for osteoblasts to migrate in from at least two sides and thus a more complete and more uniform growth can take place. A more uniform bony prominence forms, which proves overall to be conducive for the stability of the newly formed bone. This results in advantages during the insertion of implants into newly formed bone.

Thus, the invention provides a molded part which initially forms a space for blood vessels to grow into and for the subsequent ossification. The molded part serves for temporary filling or bridging of bone defects and lesions which cannot be remedied solely by the regenerative capacity of the body. At the same time the molded part can also serve as a filling element for reconstructive surgery, bone tumors or for augmentations, for example before insertion of dental implants.

By the conclusion of the treatment the molded part is completely replaced by newly formed bone substance. The components of the molded part are successively reabsorbed and thus create space in which new bone can form. Until this space is filled with bone material, the slowly degrading molded part stabilizes the newly formed bone structure.

It is regarded as advantageous if the molded part is formed from a composition which comprises at least one structuring material and consists of or comprises a granulate. The composition is not restricted to these two components but can additionally comprise further components. For production of the molded part, water, preferably distilled water, is additionally added to the composition in order to ensure the moldability. This water is either bound by the composition or evaporates in the course of drying of the finished molded part.

The structuring material is preferably selected from the group consisting of impression plaster, plaster of Paris, hard plaster, super-hard plaster, glass ionomer cement, carboxylate cement or mixtures thereof. All the aforementioned materials can be completely reabsorbed and are known from their use in the field of jaw surgery and implant medicine and are suitable for use. Plaster of Paris is preferably used, which in addition to a corresponding reabsorbability ensures a sufficient stability of the molded part or solid body during the bone growth. At the same time this material favors the growth of blood vessels. The term "plaster of Paris" is well known from dentistry. With regard to its hardness, plaster of Paris is between the impression plaster which is likewise used in the dental field and a hard plaster. After production of the molded part with simple dental tools, this plaster can be further processed and thus allows an adaptation of the solid body to the conditions in the jaw.

The molded part is also capable of absorbing and stabilizing blood clots which form. This increases the chances that blood vessels can grow simultaneously in the entire molded part. These blood vessels serve for the supply of nutrients to the osteoblasts, so that an ossification or osteogenesis can occur, during which new bone material forms and thus, for example, a jaw bone previously damaged due to periodontitis can be reconstructed.

In this case the molded part which can be completely reabsorbed by the body is permanently inherently stable and dimensioned so that the reabsorption process is concluded only after sufficient ossification or osteogenesis, i.e. when a supporting structure is no longer required. The molded part according to the invention can preferably be mass-produced in different sizes. In this case the molded part is formed in such a way that it can be used directly at or on the bone without changes, apart from minor corrections. For this purpose, the molded part is made available in different sizes and adapted to different positions for use. It is regarded as advantageous if the molded part is completely reabsorbable by the human or animal body.

Hyaluronic acid (or hyaluronic acid derivatives), which can likewise be used in the context of the present invention, has an advantageous effect on the treatment of pathological changes of the periodontium and shows positive effects on fibroblasts, bone regeneration and wound healing. In the context of the present invention hyaluronic acid (or derivatives thereof) added directly to or admixed with the composition according to the invention. Alternatively, after preparation of the molded part and during the insertion or the placing on a bone base a hyaluronic acid preparation can be added to or poured onto the operating location. In this case, hyaluronic acid has different functions.

The basic operating principle of hyaluronic acid in the context of the present invention provides that in an aqueous environment a three-dimensional mesh network is produced following a spontaneous aggregation of the hyaluronic acid chains. Cellular and fibrous components can be embedded in this network. This favors and promotes the formation of a bone structure. At the same time, hyaluronic acid has a regulating function in the organization of the extracellular matrix and its components. In this case the hyaluronic acid network which is formed is a prerequisite for the exchange of substances and serves simultaneously as a barrier against the penetration of extraneous substances. Due to the formation of the networks and the condensation thereof cells can be protected against degradation processes and hydroxyl radicals. The hyaluronic acid sheaths thus provided serve different cell types as protection against external, for example viral or bacterial, influences and thus also favors the probability of survival of the osteoblasts.

Moreover, negatively charged hyaluronic acid has the ability to bind enormous quantities of water and different plasma proteins by means of hydrogen bonds and the polar ends and thus functions as a type of "osmotic buffer" of the extracellular matrix. Hyaluronic acid also proves advantageous in controlling centers of chronic inflammation and has an anti-inflammatory potential. Hyaluronic acid also influences cellular growth factors and thus has a positive influence on cellular growth processes and thus supports the tissue regeneration. These numerous advantages are used in connection with the present invention or the composition. Surprisingly it has been shown that the regeneration of the bone or bone material can be significantly improved.

Surprisingly it has been shown that the molded part according to the present invention enables a clearly superior form of ossification or osteogenesis by comparison with the prior art.

It is regarded as advantageous if the granulate provided in the molded part or the composition is selected from a basic material selected from the group consisting of aragonite, seashell, allogenic bone material, autogenic bone material, xenogenic bone material, FDBA (freeze-dried bone allografts), DFBDA (decalcified freeze-dried bone allografts), algae or algae extract, ceramic, calcium phosphate, in particular tri- or tetracalcium phosphate, α- or β-tricalcium phosphate, hydroxylapatite, calcium phosphate ceramic, bioglass, bone replacement material based on aragonite (z.B. BioCoral®) or mixtures thereof.

In particular, it is conceivable to produce the granulate from donor bone. Granulate which is produced from bone from bone banks is also covered by the invention.

The invention also regards the use of FDBA (freeze dried bone allografts) or DFDBA (decalcified freeze dried bone allografts) as advantageous. The bone growth can proceed optimally due to the formation of the granulate from a material taken from a genetically different individual of the same species. The probability of inflammatory reactions is advantageously reduced. The use of xenogenic materials for production of the granulate also proves advantageous.

For the production of granules which are suitable for humans, bones of cattle, pigs and horses are particularly suitable. It is also possible and is covered by the invention that the granulate is formed from algae, in particular algae extracts, corals or mussels. The shells of mussels prove particularly suitable for the production of the granules, since they consist of a calcium/protein mixture, more precisely aragonite, and therefore can be reabsorbed particularly well by the body.

In addition, it is also possible to produce the granulate from autogenic material, i.e. material provided by the patient itself. For this purpose, first of all bone material is taken from the patient, is processed to form a granulate and is prepared for use in the molded part according to the invention, which is inserted or implanted into the patient in the context of further treatment. In this case the probability of the occurrence of inflammatory reactions in the patient's body is minimal.

Furthermore, it is possible to use alloplastic materials such as calcium phosphates, ceramics or bioglasses for the production of the granulate.

The basic material of the granulate preferably consists of: aragonite in combination with between 0 and 50%, in particular between 15 and 35%, preferably 25% bone material, in particular allogenic or autogenic bone material. The use of xenogenic bone material or one or more of the other above-mentioned materials is likewise possible and covered by the invention. Combinations or mixtures of different materials and use thereof in combination with aragonite are also covered.

It is advantageous if the basic material of the granulate is only formed of bone material, in particular allogenic, autogenic and/or xenogenic bone material.

The granulate preferably has a particle size of between 1 and 3 mm, in particular between 1.1 and 2 mm, preferably 1.5 mm. These particle size or particle size ranges prove optimal from the point of view of reabsorption. By a choice of the grain size adapted to the particular patient or intended use the duration and speed of reabsorption can be defined and thus the success of the treatment can be further improved. In addition to the particle size the porosity of the granulate material is also a criterion to which attention should be paid. A large number of pores or porous bodies in the granulate or on the granulate surface can substantially enlarge the surface available for the growth of blood vessels or osteoblasts and the osteoblast growth can be improved as a result. The porosity of the granulate material results on the one hand from the material itself or on the other hand can be set in a defined range by suitable pre-treatment of the granulate or granulate starting material, or by an acid treatment or similar.

It proves advantageous if a sealing material is provided between the molded part and the bone base in order to prevent the growth of blood vessels or the penetration into the molded part of substances or microorganisms which damage the bone growth. In this case the sealing material is formed in particular from collagen, preferably collagen type 1 or type 3 or a mixture of collagen type 1 and collagen type 3 and/or hyaluronic acid or hyaluronic acid derivative.

In a further embodiment of the invention which is regarded as advantageous it is provided that the composition forming the molded part contains at least one further substance. This is preferably selected from the group consisting of statins, vitamins, trace elements, antibiotics or mixtures thereof. Whilst vitamins and trace elements serve to supply the newly formed cells, statins or statin preparations facilitate the immunomodulation and thus reduce the tendency to inflammation. Antibiotics serve to control or prevent bacterial infections on or in the bone base. The invention is not limited to the aforementioned substances, but includes all substances and mixtures of substances which are familiar to the person skilled in the art and can be used in the context of the present invention.

In this connection, it has proved advantageous if the at least one further substance constitutes between 0.1 and 3%, in particular between 0.2 and 1.5%, preferably 0.25% of the composition.

According to the invention the molded part in the basic configuration is formed from the structuring material as defined above and the granulate which is likewise pre-defined. In this connection, it is regarded as advantageous if a ratio of structuring material to granulate of between 1:1 and 1:4 is provided in the molded part. A molded part which is formed from 1 part of the structuring material and 2 parts of granulate is regarded as particularly advantageous. Depending upon the intended use and the conditions at the site at which new bone is to be formed, the aforementioned ratios can of course also be set differently. The water required for the production of the moldable compound from the composition, preferably distilled and sterilized water, remains unconsidered.

Surprisingly it has been shown that a ratio of structuring material to granulate of 1:2 has proved the most successful, if it was a question of allowing a sufficiently stable bone material to grow. In addition to the structure provided by the molded part configured in this way for the bone growth or the ossification, a corresponding ratio of structuring material and granulate also ensures a temporally defined reabsorption.

The biocompatible molded part is preferably block-shaped or cuboid. In this case, understandably, there is also the possibility of forming the molded part so that it is adapted in shape to a recess in the bone, in particular the jaw bone or jaw bone portion. If a standardized molded part is made available, before it is placed on the bone this part can be adapted in its shape, that is to say in particular in its height, width and length. Thus, it is ensured that a molded part is provided which is adapted to the conditions in the patient. A further advantage is that production of a molded part having a uniform shape can be standardized and therefore cost-effective.

It is regarded as advantageous if the molded part which is block-shaped or cuboid or is adapted in its shape to a recess in the bone, in particular a jaw bone or jaw bone portion, has edges with an edge length of between 1 and 5 cm in each case. It is regarded as advantageous if the edge length is between 1.5 and 3 cm. Such a standardized molded part 1 preferably has a maximum width of 1.5 cm, a maximum height of 3 cm and a maximum height likewise of 1.5 cm. The corresponding edge lengths and the resulting size and the volume of the molded part ensure that a complete blood vessels can flow completely through it and a sufficiently stable osteogenesis can take place. Simultaneously a complete reabsorption of the molded part in the course of the healing process is achieved.

In a further embodiment of the biocompatible molded part according to the invention it is regarded as advantageous if this molded part has at least one bore. This bore serves for the passage of a fastening means, in particular a screw, which is used for fastening of the molded part on the bone. In this case the bore or the bores are already introduced into the molded part during production, i.e. modelling, of the molded part. Alternatively, there is obviously also the possibility that these bores are introduced retrospectively into the molded part using suitable tools. A previously defined or individually adapted arrangement, which is adapted to the later arrangement points of the molded part on the bone, can also be provided in the molded part.

A composition for production of the biocompatible molded part is of equal inventive significance. This comprises or consists of a structuring material and a granulate. Structuring material and granulate are mixed in defined ratios in order, after addition of water, to form a molded part from this, in particular according to the present invention.

The structuring material is preferably selected from the group consisting of impression plaster, plaster of Paris, hard plaster, super-hard plaster, glass ionomer cement, carbonlate cement or mixtures thereof. All the aforementioned materials can be completely reabsorbed and are known from their use in the field of orthopedic jaw surgery and implant medicine known and are suitable for use. Plaster of Paris is preferably used which, in addition to a corresponding reabsorbability, ensures a sufficient stability of the molded part or solid body. The term "plaster of Paris" is well known from dentistry. With regard to its hardness, plaster of Paris is between the impression plaster which is likewise used in the dental field and a hard plaster. After production of the molded part, this plaster can be further processed and thus allows an adaptation of the solid body to the conditions in the jaw with simple tools.

It is regarded as advantageous if the granulate is selected from a basic material selected from the group consisting of aragonite, seashell, allogenic bone material, autogenic bone material, xenogenic bone material, FDBA (freeze-dried bone allografts), DFBDA (decalcified freeze-dried bone allografts), algae or algae extract, ceramic, calcium phosphate, in particular tri- or tetracalcium phosphate, α- or β-tricalcium phosphate, hydroxylapatite, calcium phosphate ceramic, bioglass, bone replacement material based on aragonite (z.B. BioCoral®) or mixtures thereof.

In particular, it is conceivable to produce the granulate from donor bone. Granulate which is produced from bone from bone banks is likewise covered by the invention.

The invention also regards the use of FDBA (freeze dried bone allografts) or DFDBA (decalcified freeze dried bone allografts) as advantageous. The bone growth can proceed optimally due to the formation of the granulate from a material taken from a genetically different individual of the same species. The probability of inflammatory reactions is advantageously reduced. The use of xenogenic materials for production of the granulate also proves advantageous.

For the production of granules which are suitable for humans, bones of cattle, pigs and horses are particularly suitable. It is also possible and is covered by the invention that the granulate is produced from algae, in particular algae extracts, corals or mussels. The shells of mussels prove particularly suitable for the production of the granules, since they consist of a calcium/protein mixture, more precisely aragonite, and therefore can be reabsorbed particularly well by the body.

In addition, it is also possible to produce the granulate from autogenic material, i.e. material provided by the patient itself. For this purpose, first of all bone material is taken from the patient, is processed to form a granulate and is prepared for use in the molded part according to the invention, which is inserted or implanted into the patient in the context of further treatment. In this case the probability of the occurrence of inflammatory reactions in the patient's body is minimal.

Furthermore, it is possible to use alloplastic materials such as calcium phosphates, ceramics or bioglasses for the production of the granulate.

The granulate preferably has a particle size of between 1 and 3 mm, in particular between 1.1 and 2 mm, preferably 1.5 mm. These particle size or particle size ranges prove optimal from the point of view of reabsorption. By a choice of the grain size adapted to the particular patient or intended use the duration and speed of reabsorption can be defined and thus the success of the treatment can be further improved. In addition to the particle size the porosity of the granulate material is also a criterion to which attention should be paid. A large number of pores or porous bodies in the granulate or on the granulate surface can substantially enlarge the surface available for the growth of blood vessels or osteoblasts and the growth thereof can be improved as a result. The porosity of the granulate material results on the one hand from the material itself or on the other hand can be set in a defined range by suitable pre-treatment of the granulate or granulate starting material, or by an acid treatment or similar.

In a further embodiment of the invention which is regarded as advantageous it is provided that the composition contains at least one further substance. This is preferably selected from the group consisting of statins, vitamins, trace elements, antibiotics or mixtures thereof. Whilst vitamins and trace elements serve to supply the newly formed cells, statins or statin preparations facilitate the immunomodulation and reduce the tendency to inflammation. Antibiotics serve to control or prevent bacterial infections on or in the bone base. The invention is not limited to the aforementioned substances, but includes all substances and mixtures of substances which are familiar to the person skilled in the art and can be used in the context of the present invention.

In this connection, it has proved advantageous if the at least one further substance constitutes between 0.1 and 3%, in particular between 0.2 and 1.5%, preferably 0.25% of the composition.

The granulate or the basic material preferably has a sheathing layer made of at least one collagen, hyaluronic acid and/or hyaluronic acid derivative or mixtures thereof.

Further advantages are provided by the coating of the granulate or basic material. Thus, blood is absorbed from the patient, so that body cells are available at every site within and on the molded part. The growth of the blood vessels growing into the molded part is likewise promoted, since these blood vessels are crucial for the permanent supply of nutrients to the osteoblasts. New bone material can only form if there is a sufficient supply of nutrients.

Hyaluronic acid (or hyaluronic acid derivatives), which can likewise be used in the context of the present invention, has an advantageous effect on the treatment of pathological changes of the periodontium and shows positive effects on fibroblasts, bone regeneration and wound healing. In the context of the present invention hyaluronic acid (or derivatives thereof) is applied directly to the granulate. In this case the hyaluronic acid has different functions. The basic operating principle of the hyaluronic acid in the context of the present invention provides that in an aqueous environment a three-dimensional mesh network is produced following a spontaneous aggregation of the hyaluronic acid chains. Cellular and fibrous components can be embedded in this network. This favors and promotes the formation of a bone structure. At the same time, hyaluronic acid has a regulating function in the organization of the extracellular matrix and its components. In this case the hyaluronic acid network which is formed is a prerequisite for the exchange of substances and serves simultaneously as a barrier against the penetration of extraneous substances. Due to the formation of the networks and the condensation thereof cells can be protected against degradation processes and hydroxyl radicals. The hyaluronic acid sheaths thus provided serve different cell types as protection against external, for example viral or bacterial, influences and thus also favors the probability of survival of the osteoblasts.

Moreover, negatively charged hyaluronic acid has the ability to bind enormous quantities of water and different plasma proteins by means of hydrogen bonds and the polar ends and thus functions as a type of "osmotic buffer" of the extracellular matrix. Hyaluronic acid also proves advantageous in controlling centers of chronic inflammation and has an anti-inflammatory potential. Hyaluronic acid also influences cellular growth factors and thus has a positive influence on cellular growth processes and thus supports the tissue regeneration. These numerous advantages are used in connection with the present invention. Surprisingly, it has been shown that the regeneration of the bone or bone material can be significantly improved. Thus, a form of ossification or osteogenesis which is clearly superior by comparison with the prior art is effected, which is produced inter alia from the composition according to the invention and the hyaluronic acid contained or released in combination with the other components.

According to the invention the composition is formed from the structuring material as defined above and the granulate which is likewise pre-defined. In this connection, it is regarded as advantageous if a ratio of structuring material to granulate of between 1:1 and 1:4 is provided in the composition. A composition is regarded as particularly advantageous which is formed from one part of structuring material and two parts of granulate. Depending upon the intended use the aforementioned ratios can of course also be reversed or modified are available. Surprisingly, however, it has been shown that a ratio of structuring material to granulate in the composition of 1:2 has proved the most successful. The reabsorption of the material can be controlled by means of the defined ratio of structuring material to granulate.

Overall, however, all the components of the composition are reabsorbable by the human or animal body.

The basic material of the granulate which can be used in the composition consists of aragonite in combination with between 0 and 50%, in particular between 15 and 35%, preferably 25% bone material, in particular allogenic or autogenic bone material. The use of xenogenic bone material or one or more of the other above-mentioned materials is likewise possible and covered by the invention. Combinations of different materials and use thereof in combination with aragonite are also covered.

The invention also comprises a method for producing a biocompatible molded part. In this case the method comprises the following steps:
(i) producing a moldable modeling material by mixing the composition as previously defined. For this purpose, water, preferably distilled and sterile water, is used.
(ii) modeling the molded part as a block-shaped or cuboid molded part and
(iii) drying the molded part.

In this case the molded part is preferably produced as a standardized part and thus is particularly suitable for mass production. The molded part produced in the method can be adapted in use to the respective conditions in the patient's jaw bone.

The drying takes place at room temperature or in a special drying oven at an elevated temperature. In one embodiment of the invention burning of the molded part is provided.

The shrinking of the molded part in the course of drying is taken into account as an oversize allowance during the production/modeling.

Optionally or alternatively the method can also comprise the following steps:

(ia) determining a form of a bone structure, in particular the shape of the jaw bone or jaw bone portion in or on which the molded part is to be introduced, and (iia) modelling the molded part with reference to the determined form. In this case the shape of the jaw bone or jaw bone portion in or on which the molded part is to be introduced is deduced, for example, from an X-ray image.

Before insertion, the molded part is already adapted to the respective defective sites or produced in coordination therewith. Thus, subsequent processing of the finished molded part is circumvented and a precisely fitting molded part is provided.

In order to further improve the adaptation of the molded part, the optional creation of a negative model of the bone structure can be carried out beforehand.

In order to prevent the growth of germs and thus avoid inflammation, or in order to prevent the bacterial count, it is regarded as advantageous if the method further comprises the step (iv) of sterilizing the molded part, in particular by irradiation with gamma radiation. Naturally, heat sterilization is also possible.

The production of the molded part is substantially simplified by the use of a mold, preferably a silicone mold, for the modeling. This mold can be produced and made available in different sizes. During the production, the mold is filled with the modeling material produced from the composition according to the invention using water. After removal of the mold the molded parts are dried, optionally processed (smoothing, drilling, milling, chamfering, etc.), subsequently sterilized and then packaged.

In order to enable fastening of the molded part on the jaw or jaw bone, it is regarded as advantageous to introduce at least one through bore into the molded part before or after the drying. This/these bore(s) then serve(s) for the passage of screws by means of which the molded part is connected to the jaw. After the formation of the bone and the reabsorption of the molded part these screws can then be removed from the newly formed bone.

The invention also provides for use of a molded part as defined above. The molded part is particularly suitable for use in plastic medicine or dental medicine. The use preferably takes place according to the invention for supporting new bone formation, in particular in the jaw bone, wherein the molded part bone stabilizes the newly forming bone and subsequently or during the new bone formation is completely reabsorbed and replaced by newly formed bone.

In this connection, the use of the molded part for bone augmentation of an existing bone structure is regarded as advantageous. In this case, in particular a bone augmentation of up to approximately 1.5 cm is possible.

When the molded part is used, it is regarded as advantageous if adaptation of the length, width and/or height of the molded part is carried out before use.

The invention also comprises a kit which comprises a plurality of molded parts as described above. In this case the molded parts preferably have the same or different sizes and/or shapes. Thus, in use the most suitable molded part can be selected from the kit and can be used for the augmentation of the jaw bone. In this case the molded part which is most suitable from the point of view of size and shape can be selected and then an adaptation of the length, width and/or height of the molded part can be carried out before the part is used. The reworking of the prefabricated molded part then takes place using conventional tools. The size can be adapted by simple abrasion of excess material.

The kit according to the invention enables the user to select the most suitable molded part, so that the need for adaptation is only very low.

EXAMPLE

The advantageous ossification or osteogenesis induced by the molded part according to the invention could be demonstrated in the animal experiment. In the animal experiment block-shaped molded parts, designated hereafter as molded part 1 or molded part 2 were implanted on the calvaria of three pigs.

In this case the molded parts had the following features:
molded part A:
weight: approximately 15 g
composition:
⅔ plaster as structuring material
⅓ granulate according to the invention
dimensions of the molded part:
length: 2 cm
width: 1 cm
height: 1.5 cm
molded part B:
weight: approximately 15 g
composition:
⅔ carbon/late cement as structuring material
⅓ granulate according to the invention
dimensions of the molded part:
length: 2 cm
width: 1 cm
height: 1.5 cm The above-mentioned molded parts were implanted on the calvaria of three pigs. Molded part A on the left-hand side, molded part B on the right-hand side of the respective animal. For fastening the molded parts to the calvaria, bores were introduced into the calvaria. These bores served for the passage of screws by means of which the molded parts were screwed to the calvaria.

After 8 weeks, the animals were sacrificed and the implanted sites were examined histologically.

Result:

At the sites where the molded part A was implanted the degradation of the material and the reabsorption thereof had started. Simultaneously there was detectable bone regeneration or new bone formation. Good healing and a vertical increase in height could be seen. In the bone which has formed, the screws 6 are surrounded by bone material.

During the time of the experiment, at the sites where the molded part B was implanted there was a reduction or even an absence of degradation of the material. Also, no bone regeneration or new bone formation could be detected there. Some disorders of wound healing occurred.

Figure 2:
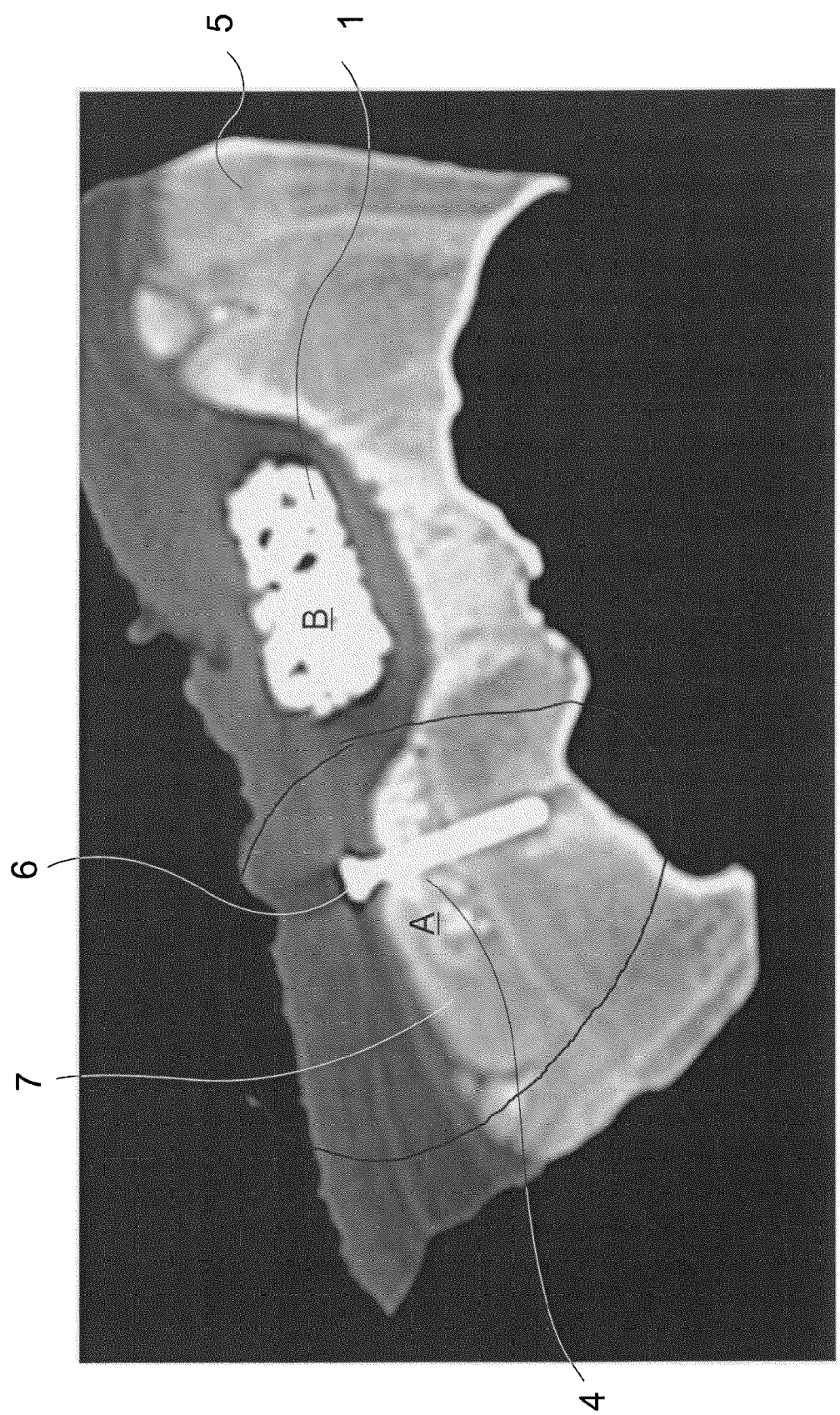

Further advantages and expedient embodiments can be seen from following description of the figures and from the drawings. In the drawings:

FIG. 1 shows a schematic representation of a preferred embodiment of a molded part, and FIG. 2 shows the evaluation by computer tomography of the illustrative experiment described above.

The molded part 1 is shown in perspective in FIG. 1. At the top the molded part 1 has a rounding 2 which is adapted to the shape of the jaw bone. The further end surfaces 3 of the molded part 1 are at right angles with respect to one another. This results in a block-shaped or cuboid molded part 1. This molded part 1 illustrated here as a standard element can be adapted before use to the particular conditions in the patient's jaw. As a result, the end surfaces 3 are correspondingly trimmed or abraded. In this case the size of the molded part 1 can also be adapted. In the embodiment illustrated in FIG. 1 the molded part 1 has a length of 3 cm, a height of 1.5 cm and a width of likewise 1.5 cm. The molded part 1 is formed from a composition which is produced from plaster of Paris and a granulate formed from a bone material. The composition was mixed with distilled water until a compound with a moldable consistency was produced. Next a silicone mold was filled with the modeling material. This silicone mold has the shape of the finished molded part 1. After removal from the mold the molded part 1 was dried. The shrinkage of the material during drying was taken into account in the dimensioning of the silicone mold. After sterilization and packaging the molded part 1 was available for use. Final processing of the molded part 1 takes place before it is inserted or placed on the jaw bone. In addition, two bores 4 are provided in the molded part. Through these bores 4 the molded part 1 can be fastened by means of bone screws to the jaw bone (not shown). After reabsorption of the molded part 1 and conclusion of the new bone formation the screws can be removed again from the jaw. The remaining apertures are, for example, filled with a material which also promotes osteogenesis and subsequently ossified.

In order to prevent cells of the periosteum or cells of the gingiva from penetrating adversely into the molded part 1, the molded part 1 can be sealed with respect to the surrounding teeth with the aid of collagen.

In order to attach the molded part 1 to the jaw bone, first of all the upper flap of gingiva is folded back. The surface of the jaw bone is optionally roughened in order to promote the growth of the bone. Then the molded part 1 is applied to the corresponding location and is fixed to the jaw bone by pins or screws. Then the flap of gingiva is folded over the molded part 1 and fixed to the outer face of the molded part 1. The periosteum then grows along the outer face of the molded part 1, so that after some time the original jaw situation with complete jaw bone, periosteum and gingiva is restored. A second operation for removal of the molded part 1 after new bone formation has taken place is not necessary, since the molded part 1 is completely degraded by the body.

Blood vessels and bone cells grow into the molded part 1 and little by little they pass through it completely. As this happens the jaw bone is successively remodeled. Overall the inserted molded part 1 provides a structure which serves as a base or framework for the formation of new blood vessels. Ultimately this base leads to a new bone formation if osteoblasts have a sufficient supply of nutrients in order to form new bone material. The molded part 1 is completely reabsorbed by the body. The entire insertion site of the molded part 1 can be washed with a hyaluronic acid solution which favors the blood vessel growth in the first growth phase.

FIG. 2 shows the evaluation by computer tomography of the illustrative experiment described above.

The implantation site of the molded part A 1 on the calvaria 5 of a pig can be seen and identified on the left in FIG. 2. The molded part B 1 is shown on the right in FIG. 2. For fastening the molded parts 1 to the calvaria 5, bores 4 have been introduced into the calvaria. These bores 4 serve for the passage of screws 6 which can still be seen in the CT image and by means of which the molded parts 1 are screwed to the calvaria 5.

FIG. 2 shows the result after the experiment has been running for 8 weeks. At the site where the molded part A 1 was implanted the degradation of the material of the molded part 1 and the reabsorption thereof has started. Simultaneously there has been detectable bone regeneration or new bone formation. Good healing and a vertical increase in height can be seen. In the bone 7 which has formed the screws 6 are surrounded by bone material.

During the time of the experiment, at the sites where the molded part B 1 was implanted there was a reduction or even an absence of degradation of the material. Also, no bone regeneration or new bone formation could be detected there. Some disorders of wound healing occurred.

The invention comprises:

A biocompatible molded part for supporting new bone formation, in particular the reformation of a jaw bone or a jaw bone portion in a mammal, preferably a human, wherein the molded part is suitable to be placed on the jaw bone and is designed as a solid body.

A biocompatible molded part configured as above, wherein the molded part is formed from a composition comprising or consisting of at least one structuring material and a granulate.

A biocompatible molded part configured as above, wherein the structuring material is selected from the group consisting of impression plaster, plaster of Paris, hard plaster, super-hard plaster, glass ionomer cement, carbon/late cement or mixtures thereof, preferably plaster of Paris.

A biocompatible molded part configured as above, wherein the granulate is formed from a basic material selected from the group consisting of: aragonite, seashell, allogenic bone material, autogenic bone material, xenogenic bone material, FDBA (freeze-dried bone allografts), DFBA (decalcified freeze-dried bone allografts), algae or algae extract, ceramic, calcium phosphate, in particular tri- or tetracalcium phosphate, α- or β-tricalcium phosphate, hydroxylapatite, calcium phosphate ceramic, bioglass, bone replacement materials based on aragonite (e.g. BioCoral®) or mixtures thereof.

A biocompatible molded part configured as above, wherein the granulate has a particle size of between 1 and 3 mm, in particular between 1.1 and 2 mm, preferably 1.5 mm.

A biocompatible molded part configured as above, wherein in the composition the structuring material and the granulate are provided in a ratio of between 1:1 and 1:4, preferably 1:2.

A biocompatible molded part configured as above, wherein the composition contains at least one further substance, in particular wherein the at least one further substance is selected from the group consisting of statins, vitamins, trace elements, antibiotics hyaluronic acid, hyaluronic acid derivatives, collagen and/or mixtures thereof, in particular wherein the at least one further substance constitutes between 0.1 and 3%, in particular between 0.2 and 1.5%, preferably 0.25% of the composition.

A biocompatible molded part configured as above, wherein the solid body is completely reabsorbable by the human or animal body.

A biocompatible molded part configured as above, wherein the basic material of the granulate consists of:
  aragonite and
  0-50%, in particular between 15 and 35%, preferably 25% bone material, in particular allogenic or autogenic bone material.

A biocompatible molded part configured as above, wherein a sealing material is provided between the molded part and the jaw bone or the bone base, in particular wherein the sealing material is formed from a collagen, in particular collagen type 1 or a mixture of collagen type 1 and collagen type 3 and hyaluronic acid or hyaluronic acid-derivative.

A biocompatible molded part configured as above, wherein the molded part is substantially block-shaped or cuboid or is adapted in shape to a recess in the bone, in particular the jaw bone or jaw bone portion.

A biocompatible molded part configured as above, wherein the molded part is substantially block-shaped or cuboid and is adapted in shape to a recess in the bone, in particular the jaw bone or jaw bone portion.

A biocompatible molded part configured as before, wherein the molded part which is substantially block-shaped or cuboid or is adapted in shape to a recess in the bone, in particular a jaw bone or jaw bone portion, has edges with an edge length in each case of between 1 and 5 cm, preferably between 1.5 and 3 cm.

A biocompatible molded part configured as above, wherein the molded part which is substantially block-shaped or cuboid or is adapted in shape to a recess in the bone, in particular the jaw bone or jaw bone portion, is provided with at least one bore for the passage of fastening means, in particular screws.

Furthermore, the invention comprises a composition for production of a biocompatible molded part as defined above, comprising or consisting of a structuring material and a granulate.

A composition configured as above, wherein the structuring material is selected from the group consisting of impression plaster, plaster of Paris, hard plaster, super-hard plaster, glass ionomer cement, carboxylate cement or mixtures thereof, preferably plaster of Paris.

A composition configured as above, wherein the granulate is formed from a basic material selected from the group consisting of: Aragonite, seashell, allogenic bone material, autogenic bone material, xenogenic bone material, FDBA (freeze-dried bone allografts), DFBA (decalcified freeze-dried bone allografts), algae or algae extract, ceramic, calcium phosphate, in particular tri- or tetracalcium phosphate, α- or β-tricalcium phosphate, hydroxylapatite, calcium phosphate ceramic, bioglass, bone replacement material based on aragonite (e.g. BioCoral®) or mixtures thereof.

A composition configured as above, wherein the granulate or the basic material preferably has a sheathing layer made of at least one collagen, hyaluronic acid and/or hyaluronic acid derivative or mixtures thereof.

A composition configured as above, wherein the granulate has a particle size of between 1 and 3 mm, in particular between 1.1 and 2 mm, preferably 1.5 mm.

A composition configured as above, wherein in the composition the structuring material and the granulate are provided in a ratio of between 1:1 and 1:4, preferably 1:2.

A composition configured as above, wherein the composition contains at least one further substance, in particular wherein the at least one further substance is selected from the group consisting of statins, vitamins, trace elements, antibiotics or mixtures thereof, in particular wherein the at least one further substance constitutes between 0.1 and 3%, in particular between 0.2 and 1.5%, preferably 0.25% of the composition.

A composition configured as above, wherein a complete reabsorbability of the components by the human or animal body is provided.

A composition configured as above, wherein the basic material of the granulate consists of:
aragonite and
0-50%, in particular between 15 and 35%, preferably 25% bone material, in particular allogenic or autogenic bone material.

The invention also comprises a method for producing a biocompatible molded part, in particular a molded part defined as above, comprising the steps:
(iv) producing a moldable modeling material by mixing the composition as defined in claims 12 to 20 with water, preferably distilled water,
(ii) modeling the molded part as a block-shaped or cuboid molded part and
(iii) drying the molded part.

The method referred to above, alternatively comprising the steps:
(ia) determining a form of a bone structure, in particular the shape of the jaw bone or jaw bone portion in or on which the molded part is to be introduced, and (iia) modeling the molded part with reference to the determined form.

The method referred to above, optionally comprising the step:
(ib) creation of a negative model of the bone structure.

The method referred to above, further comprising (iv) sterilizing the molded part, in particular by irradiation with gamma radiation.

The method referred to above, wherein the modeling of the molded part takes place using a mold.

The method referred to above, wherein at least one through bore is introduced into the molded part before or after the drying.

The invention also comprises a use of a biocompatible molded part as defined above, formed from the composition referred to above and produced according to the aforementioned method, in medicine, in particular in plastic medicine or dental medicine, preferably for supporting a new bone formation, in particular in the jaw bone, wherein the biocompatible molded part provides a basic structure for the new bone formation and is completely reabsorbed in the course of new bone formation.

The aforementioned use, for bone augmentation of an existing bone structure.

The aforementioned use, wherein an adaptation of the length, width and/or height of the molded part is provided before use.

The invention also comprises a kit comprising a plurality of molded parts as defined above.

The aforementioned kit, wherein the molded parts have the same or different sizes and/or shapes.

The aforementioned kit, wherein an adaptation of the length, width and/or height of the molded part is provided before use.

The claims filed now with the application and later are attempts at formulation without prejudice for the achievement of more far-reaching protection.

If closer examination, in particular also of the relevant prior art, reveals that one or the other feature is favorable for the object of the invention, but is not crucially important, then of course a formulation will be sought which no longer includes such a feature, in particular in the main claim.

It should also be noted that the configurations and variants of the invention described in the various embodiments and illustrated in the drawings can be combined with one another in any way. In this case individual features or a plurality of features are interchangeable with one another in any way. These combinations of features are also disclosed.

The dependencies set out in the dependent claims refer to the further embodiment of the subject matter of the main claim by the features of the respective subordinate claim. However, these are not to be understood as a renunciation of the achievement of independent objective protection for the features of the dependent subordinate claims.

In the course of the proceedings features which hitherto have only been disclosed in the description may be claimed as of essential significance to the invention, for example for differentiation from the prior art, claimed are being.

Features which have only been disclosed in the description or also individual features from claims which include a plurality of features can be incorporated into claim 1 in order to distinguish them over the prior art at any time, even when such features have been mentioned in connection with other features or also achieve particularly favorable results in connection with other features.

The invention claimed is:

1. A biocompatible molded part for supporting new bone formation in a mammal body, comprising:
    a solid body having a plurality of end surfaces arranged at right angles with respect to one another and having a rounded surface, the plurality of end surfaces defining a plurality of edges each having an edge length between 1 cm and 5 cm, the body being completely resorbable by the mammal body,
    wherein the body comprises a composition of at least one structuring material and at least one porous granulate in a ratio.

2. The biocompatible molded part of claim 1, wherein the plurality of end surfaces comprises four end surfaces.

3. The biocompatible molded part of claim 2, wherein the plurality of edges comprises seven edges.

4. The biocompatible molded part of claim 1, wherein the rounded surface extends from a first end surface of the plurality of end surfaces to an adjacent end surface of the plurality of end surfaces.

5. The biocompatible molded part of claim 4, wherein the rounded surface is adapted to a shape of a jaw bone.

6. The biocompatible molded part of claim 1, wherein the porous granulate has a particle size between 1 and 3 mm.

7. The biocompatible molded part of claim 1, wherein the ratio comprises between 1:1 and 1:4.

8. The biocompatible molded part of claim 1, wherein the body defines at least one bore configured to receive a bone screw.

9. A biocompatible molded part for supporting new bone formation in a mammal body, comprising:
    a block-shaped or cuboid solid body having a plurality of end surfaces arranged at right angles with respect to one another and having a rounded surface, the plurality of end surfaces defining a plurality of edges each having an edge length between 1 cm and 5 cm, the body being completely resorbable by the mammal body,
    wherein the body comprises a composition of at least one structuring material and at least one porous granulate in a ratio.

10. The biocompatible molded part of claim 9, wherein the plurality of end surfaces comprises four end surfaces.

11. The biocompatible molded part of claim 10, wherein the plurality of edges comprises seven edges.

12. The biocompatible molded part of claim 9, wherein the rounded surface extends from a first end surface of the plurality of end surfaces to an adjacent end surface of the plurality of end surfaces.

13. The biocompatible molded part of claim 12, wherein the rounded surface is adapted to a shape of a jaw bone.

14. The biocompatible molded part of claim 9, wherein the porous granulate has a particle size between 1 and 3 mm.

15. The biocompatible molded part of claim 9, wherein the ratio comprises between 1:1 and 1:4.

16. The biocompatible molded part of claim 9, wherein the body defines at least one bore configured to receive a bone screw.

17. A biocompatible molded part for supporting new bone formation in a mammal body, comprising:
    a block-shaped or cuboid solid body having four end surfaces arranged at right angles with respect to one another and having a rounded surface, the four end surfaces defining seven edges each having an edge length between 1 cm and 5 cm, the rounded surface extending from a first end surface of the four end surfaces to a second end surface of the four end surfaces, the body being completely resorbable by the mammal body,
    wherein the body comprises a composition of at least one structuring material and at least one porous granulate in a ratio.

18. The biocompatible molded part of claim 17, wherein the first end surface is adjacent to the second end surface.

19. The biocompatible molded part of claim 17, wherein the rounded surface is adapted to a shape of a jaw bone.

20. The biocompatible molded part of claim 17, wherein the ratio comprises between 1:1 and 1:4.

* * * * *